United States Patent [19]

Tuunanen et al.

[11] Patent Number: 5,216,488
[45] Date of Patent: Jun. 1, 1993

[54] METHOD FOR PHOTOMETRICALLY MEASURING LIGHT TRANSMITTED TO AND THROUGH CUVETTES DISPOSED IN A ROW

[75] Inventors: Jukka Tuunanen, Helsinki; Aimo Kainiemi, Espoo, both of Finland

[73] Assignee: Labsystems OY, Helsinki, Finland

[21] Appl. No.: 780,958

[22] Filed: Oct. 23, 1991

[30] Foreign Application Priority Data

Oct. 31, 1990 [FI] Finland .................... 905381

[51] Int. Cl.⁵ .................... G01N 21/00; G01N 21/59
[52] U.S. Cl. .................... 356/440; 250/576; 356/436
[58] Field of Search ............ 356/436, 440, 441, 442, 356/250; 250/227.26, 576; 359/234, 235, 236

[56] References Cited

U.S. PATENT DOCUMENTS

| | | | |
|---|---|---|---|
| 3,539,777 | 11/1970 | Rohland | 356/71 X |
| 4,004,150 | 1/1977 | Natelson | 250/576 X |
| 4,452,759 | 6/1984 | Takekawa | 356/442 X |
| 4,498,780 | 2/1985 | Banno et al. | 356/440 X |
| 4,968,148 | 11/1990 | Chow et al. | 356/436 X |
| 5,073,029 | 12/1991 | Eberly et al. | 356/436 |

FOREIGN PATENT DOCUMENTS

| | | |
|---|---|---|
| 0062160 | 3/1982 | European Pat. Off. |
| 55-44969 | 3/1980 | Japan .................... 356/319 |
| 1192008 | 5/1970 | United Kingdom . |
| 1340811 | 12/1973 | United Kingdom . |

Primary Examiner—Vincent P. McGraw
Attorney, Agent, or Firm—Hopgood, Caliamfde, Kalil, Blaustein & Judlowe

[57] ABSTRACT

The invention relates to a method and apparatus for conducting light onto cuvettes in a photometer. Onto each cuvette in a row, there is successively conducted light through a moving light-cutting disc (8), which is provided with a slot (10) at each light path. Thus the light passing through the adjacent cuvette does not disturb the measurement.

8 Claims, 1 Drawing Sheet

METHOD FOR PHOTOMETRICALLY MEASURING LIGHT TRANSMITTED TO AND THROUGH CUVETTES DISPOSED IN A ROW

The invention relates to photometers where the amount of light passing through cuvettes arranged in a row is measured. In particular the invention relates to the distribution of light in the cuvettes.

In the prior art there are known photometers, particularly designed to be used in clinical analyses, where the samples under measurement are placed in a matrix-form cuvette assembly comprising 8×12 cuvettes, which is made of transparent plastic throughout. The absorbence is measured row by row, so that from a common light source, light is conducted via separate light paths to each cuvette, and further to respective detectors.

A problem in the above described apparatuses is that the light emissions passing through adjacent channels disturb each other in the measurement.

The main object of the present invention is to solve the said problem. This is achieved by means of the methods described in the appended patent claims.

Figure 1:
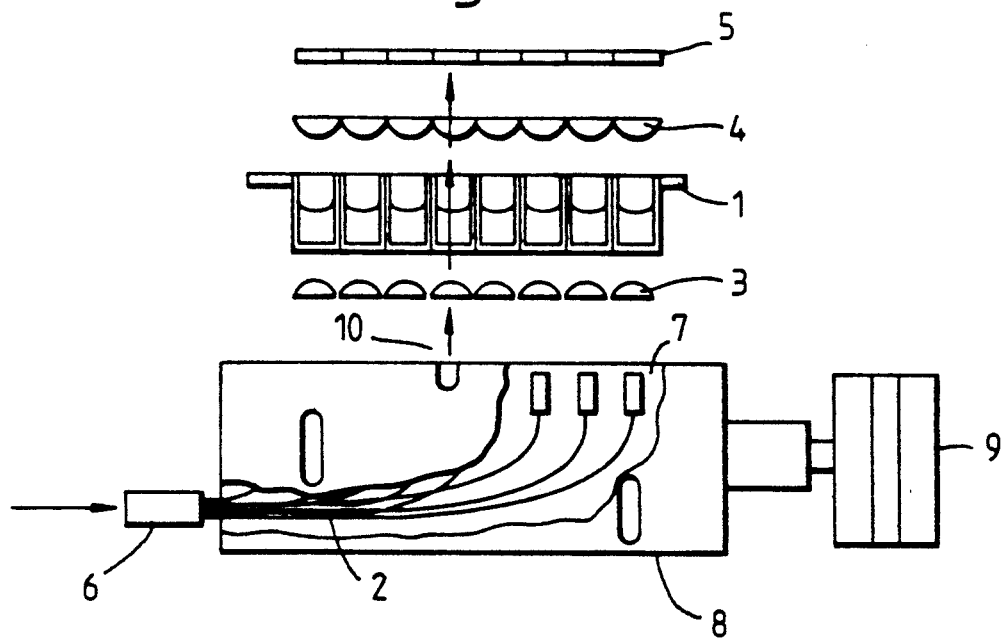
Figure 2:
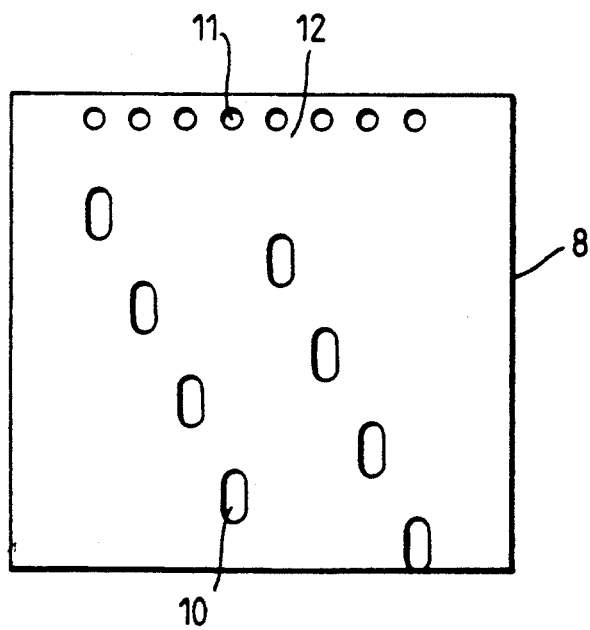

In the drawings of the specification, FIG. 1 illustrates an arrangement for conducting light through the cuvette assembly using a movable light-cutting surface, e.g., a cylinder, and FIG. 2 illustrates a light distribution light-cutting disc or plate to be employed in the arrangement.

The arrangement of the drawings is carried out in an 8-channel photometer, where the employed cuvette assembly can be a regular 8×12 microtitration plate. When carrying out the measurement, a row 1 of eight cuvettes is brought to the measuring position, where light is conducted by means of light fibers 2, through lower lenses 3, to each cuvette from below. Above the cuvettes, the light that has passed through each cuvette is collected, by means of upper lenses 4, to detectors 5. The first ends of the fibers 2 are collected by an input collar 6 to form a beam of rays, whereto the emission from the light source is conducted. From each fiber, the light passes through a collar 7 vertically upwards to each cuvette.

The outlet collars 7 of the fibers 2 are located inside a horizontal cylinder 8, which is open at one end. The cylinder is made of some material impermeable to light. The cylinder is rotated at an even velocity by means of a motor 9. In the cylinder barrel, there is made a slot 10, parallel to the barrel circumference, at each outlet collar. Thus light is emitted onto the cuvette only when the slot corresponding to the cuvette in question is located at the respective outlet collar. The length of the slot, and the speed of rotation of the cylinder, are so matched that light is emitted onto the cuvette for the duration required by the measurement.

The slots 10 are located and prearranged on the cylinder barrel in succession, at even intervals, so that light is essentially transmitted to one cuvette at a time. This prevents the light scattered from the measuring beam of one cuvette from disturbing the measurement of another cuvette. Moreover, the slots are placed or prearranged so that successive emissions of light fall on cuvettes that are located as far as possible or spaced apart from each other (note the surface in FIG. 2). Thus successive measurements can, in order to save time, be somewhat overlapping (for instance about 10% of the measuring period of each cuvette) without remarkable errors being caused by scattered light. The time used in the measurement of one plate (transmissions included) is typically about 5.5 s.

Moreover, the surface of the cylinder is provided with holes 11 for each cuvette, these holes being placed in a straight row. The holes are meant to be used particularly in the measurement of agglutinations, in which case the measuring beam is allowed to scan over the bottom by moving the cuvette assembly.

Further, the cylinder comprises surface area 12 for defining the signal obtained from the detectors in cases where no light enters the cuvette.

The apparatus is synchronized so that when, after the measurement of one row 1 on the plate, the next row is shifted to the measuring position, the cylinder 8 makes one revolution.

In principle the measurement can can also be carried out without stopping the cuvette assembly. In that case, however, measuring accuracy is reduced owing to the vibration of the liquid surface.

Instead of a rotating cylinder, there can be employed a light-cutting rectangular disc or plate moving with respect to the cuvette assembly; or a light-cutting disc rotating underneath an immobile cuvette assembly, in which disc or plate the light-permeable slots are formed.

We claim:

1. A method for transmitting measuring light from a single light source to and through cuvettes arranged in a row in a photometer, wherein the light emitted from said single light source is transmitted, via separate light paths at given durations, to each cuvette in said row, while the light passing through each cuvette is detected by a detector paired with said each cuvette in order to measure the amount of absorbance of said light, said method comprising, transmitting light in succession from said single light source to each cuvette in said row at substantially equal intervals; said light being controllably transmitted to each of said cuvettes by means of a light-cutting movable surface which intercepts said light paths; said surface being impermeable to said light except for the provision of a plurality of prearranged light-transmitting slots; each slot being arranged on said surface to correspond to a particular light path and corresponding cuvette, said slots being arranged parallel to the moving direction of the surface; and the measuring said transmitted light as it passes through a specified cuvette when a corresponding slot coordinates in position with a light path selective to said cuvette.

2. The method of claim 1, wherein said light is transmitted through separate light paths essentially to one cuvette of the row at a time.

3. The method of claim 1 or 2, wherein said light is conducted successively to cuvettes which are spaced apart from each other.

4. An apparatus for conducting measuring light successively to and through cuvettes arranged in a row in a photometer comprising a light source with a plurality of light paths coordinated therewith such as to provide a separate light path for each cuvette in said row for conducting light form the light source successively through separate light paths to and through a selected cuvette; and a detector for each of said cuvette detecting the light passing through the cuvette, said apparatus comprising a light-cutting movable surface for interpreting said light paths, said surface being movable across said light paths and being impermeable thereto except for the provision of pre-arranged light-transmitting slots disposed parallel to the moving direction of said surface, to thereby transmit light through each of a succession of slots in said surface to and through a corresponding cuvette in succession for substantially equal periods of time.

5. The apparatus of claim 4, wherein each light path comprises an optical fiber for conducting the light from the light source to a transmitting end thereof and from there to and through a corresponding cuvette, with the light-cutting surface located between the transmitting ends of the optical fibers and said cuvettes.

6. The apparatus of claim 4 or 5, wherein the light-cutting surface is a cylinder.

7. The apparatus of claim 4, wherein the light-cutting surface is also provided with a number of pre-arranged light-transmitting holes for conducting light to all of the cuvettes simultaneously.

8. The apparatus of claim 4 or 5, wherein said surface is a movable disc or plate.

* * * * *

UNITED STATES PATENT AND TRADEMARK OFFICE
CERTIFICATE OF CORRECTION

PATENT NO. : 5,216,488
DATED : June 1, 1993
INVENTOR(S) : Tuunanen, et al.

It is certified that error appears in the above-indentified patent and that said Letters Patent is hereby corrected as shown below:

Claim 1, col. 2, line 45, before "measuring" delete "the" and insert --then-- in its place Claim 4, col. 2, line 60, change "form" to --from--

Claim 4, col. 2, lines 64-65 change "interpreting" to --intercepting--

Signed and Sealed this

Twenty-fifth Day of January, 1994

Attest:

BRUCE LEHMAN

Attesting Officer

Commissioner of Patents and Trademarks